US00H002070H

(19) United States

(12) Statutory Invention Registration (10) Reg. No.: US H2070 H

Hoskins et al. (43) Published: Jul. 1, 2003

(54) *STREPTOCOCCUS PNEUMONIAE* GENE SEQUENCE FOR DNA LIGASE

(75) Inventors: Jo Ann Hoskins, Indianapolis, IN (US); Stanley Richard Jaskunas, Jr., Natick, MA (US); Timothy Ivan Meier, Franklin, IN (US); Pamela Kay Rockey, Franklin, IN (US); Genshi Zhao, Indianapolis, IN (US)

(73) Assignee: Eli Lilly and Company, Indianapolis, IN (US)

(21) Appl. No.: 08/987,119

(22) Filed: Dec. 8, 1997

Related U.S. Application Data

(60) Provisional application No. 60/036,281, filed on Dec. 13, 1996.

(51) Int. Cl.[7] ..... C12N 15/31; C12N 15/63; C12N 1/21

(52) U.S. Cl. ..... 435/69.1; 435/320.1; 435/252.3; 536/23.7; 536/23.1

(58) Field of Search ..... 536/23.1, 23.7; 435/69.1, 71.2, 320.1, 252.3

(56) References Cited

PUBLICATIONS

Rudinger In "Peptide Hormones" (ed. J.A. Parsons) University Park Press, Baltimore, pp. 1–7, 1976.*

E. Bruce Konrad, et al. "Genetic and Enzymatic Characterization of a Conditional Lethal Mutant of *Escherichia coli* K12 with a Temperature–sensitive DNA Ligase" *J. Mol. Biol.* 77:519–529 (1973).

Yoshizumi Ishino, et al. "Nucleotide sequence of the lig gene and primary structure of DNA ligsase of *Escherichia coli" Mol. Gen. Genet.* 204:1–7 (1986).

Lawrence S. Morse and Crellin Pauling. "Induction of error–prone repair as a consequence of DNA ligase deficiency in *Escherichia coli" Proc. Nat. Acad. Sci.* 72(11):4645–4649 (Nov. 1975).

James J. Dermody, et al. "Conditional–Lethal Deoxyribonucleic Acid Ligase Mutant of *Escherichia coli" Journal of Bacteriology* 139(2): 701–704 (Aug. 1979).

Takashi Sato, et al. "Genetic Analyses of an Amber Mutation in *Escherichia coli* K–12, Affecting Deoxyribonucleic Acid Ligase and Viability" *Journal of Bacteriology* 124(3): 1089–1096 (Dec. 1975).

* cited by examiner

*Primary Examiner*—Michael J. Carone
*Assistant Examiner*—Aileen J. Baker
(74) *Attorney, Agent, or Firm*—Thomas D. Webster; Raymond S. Parker, III; Charles E. Cohen

(57) ABSTRACT

The invention provides isolated nucleic acid compounds encoding a DNA ligase of *Streptococcus pneumoniae.* Also provided are vectors and transformed host cells for expressing the encoded protein, and a method for identifying compounds that bind and/or inhibit said protein.

22 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

*STREPTOCOCCUS PNEUMONIAE* GENE SEQUENCE FOR DNA LIGASE

This application claims the benefit of U.S. provisional application No. 60/036,281, filed Dec. 13, 1996.

BACKGROUND OF THE INVENTION

This invention provides isolated DNA sequences, proteins encoded thereby, and methods of using said DNA and protein in a variety of applications.

Widespread antibiotic resistance in common pathogenic bacterial species has justifiably alarmed the medical and research communities. Frequently, resistant organisms are co-resistant to several antibacterial agents. Penicillin resistance in *Streptococcus pneumoniae* has been particularly problematic. This organism causes upper respiratory tract infections. Modification of a penicillin-binding protein (PBP) underlies resistance to penicillin in the majority of cases. Combating resistance to antibiotic agents will require research into the molecular biology of pathogenic organisms. The goal of such research will be to identify new antibacterial agents.

While researchers continue to develop antibiotics effective against a number of microorganisms, *Streptococcus pneumoniae* has been more refractory. In part, this is because *Streptococcus pneumoniae* is highly recombinogenic and readily takes up exogenous DNA from its surroundings. Thus, there is a need for new antibacterial compounds and new targets for antibacterial therapy in *Streptococcus pneumoniae.*

BRIEF SUMMARY OF THE INVENTION

The present invention relates to an isolated gene and encoded protein from *S. pneumoniae.* The invention enables: (1) preparation of probes and primers for use in hybridizations and PCR amplifications, (2) production of proteins and RNAs encoded by said gene and related nucleic acids, and (3) methods to identify compounds that bind and/or inhibit said protein(s).

In one embodiment the present invention relates to an isolated nucleic acid molecule encoding a DNA ligase protein.

In another embodiment, the invention relates to a nucleic acid molecule comprising the nucleotide sequence identified as SEQ ID NO:1, SEQ ID NO:3, SEQ ID NO:4, or SEQ ID NO:5.

In another embodiment, the present invention relates to a nucleic acid that encodes SEQ ID NO:2.

In another embodiment the present invention relates to an isolated protein molecule, wherein said protein molecule comprises the sequence identified as SEQ ID NO:2.

In yet another embodiment, the present invention relates to a recombinant DNA vector that incorporates the Ligase gene (viz. "Lig") in operable linkage to gene expression sequences enabling the gene to be transcribed and translated in a host cell.

In still another embodiment the present invention relates to host cells that have been transformed or transfected with the cloned Lig gene such that the Lig gene is expressed in the host cell.

This invention also provides a method of determining whether a nucleic acid sequence of the present invention, or fragment thereof, is present in a sample, comprising contacting the sample, under suitable hybridization conditions, with a nucleic acid probe of the present invention.

In a still further embodiment, the present invention relates to a method for identifying compounds that bind and/or inhibit the Lig protein.

DETAILED DESCRIPTION OF THE INVENTION

"ORF" (i.e. "open reading frame") designates a region of genomic DNA beginning with a Met or other initiation codon and terminating with a translation stop codon, that potentially encodes a protein product. "Partial ORF" means a portion of an ORF as disclosed herein such that the initiation codon, the stop codon, or both are not disclosed.

"Consensus sequence" refers to an amino acid or nucleotide sequence that may suggest the biological function of a protein, DNA, or RNA molecule. Consensus sequences are identified by comparing proteins, RNAs, and gene homologues from different species.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

"Essential genes" or "essential ORFs" or "essential proteins" refer to genomic information or the protein(s) or RNAs encoded thereby, that when disrupted by knockout mutation, or by other mutation, result in a loss of viability of cells harboring said mutation.

"Non-essential genes" or "non-essential ORFs" or "non-essential proteins" refer to genomic information or the protein(s) or RNAs encoded therefrom which when disrupted by knockout mutation, or other mutation, do not result in a loss of viability of cells harboring said mutation.

"Minimal gene set" refers to a genus comprising about 256 genes conserved among different bacteria such as *M. genitalium* and *H. influenzae.* The minimal gene set may be necessary and sufficient to sustain life. See e.g. A. Mushegian and E. Koonin, "A minimal gene set for cellular life derived by comparison of complete bacterial genomes" Proc. Nat. Acad. Sci. 93, 10268–273 (1996).

"Knockout mutant" or "knockout mutation" as used herein refers to an in vitro engineered disruption of a region of native chromosomal DNA, typically within a protein coding region, such that a foreign piece of DNA is inserted within the native sequence. A knockout mutation occurring in a protein coding region prevents expression of the wild-type protein. This usually leads to loss of the function provided by the protein. A "knockout cassette" refers to a fragment of native chromosomal DNA having cloned therein a foreign piece of DNA that may provide a selectable marker.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refer to the capacity of purine and pyrimidine nucleotides to associate through hydrogen bonding to form double stranded nucleic acid molecules. The following base pairs are related by complementarity: guanine and cytosine; adenine and thymine; and adenine and uracil. As used herein, "complementary" applies to all base pairs comprising two single-stranded nucleic acid molecules. "Partially complementary" means one of two single-stranded nucleic acid molecules is shorter than the other, such that one of the molecules remains partially single-stranded.

"Oligonucleotide" refers to a short nucleotide chain comprising from about 2 to about 25 nucleotides.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which can be used to hybridize with another nucleic acid compound.

The term "hybridization" or "hybridize" as used herein refers to the process by which a single-stranded nucleic acid molecule joins with a complementary strand through nucleotide base pairing.

"Substantially purified" as used herein means a specific isolated nucleic acid or protein, or fragment thereof, in which substantially all contaminants (i.e. substances that differ from said specific molecule) have been separated from said nucleic acid or protein. For example, a protein may, but not necessarily, be "substantially purified" by the IMAC method as described herein.

"Selective hybridization" refers to hybridization under conditions of high stringency. The degree of hybridization between nucleic acid molecules depends upon, for example, the degree of complementarity, the stringency of hybridization, and the length of hybridizing strands.

The term "stringency" relates to nucleic acid hybridization conditions. High stringency conditions disfavor non-homologous base pairing. Low stringency conditions have the opposite effect. Stringency may be altered, for example, by changes in temperature and salt concentration. Typical high stringency conditions comprise hybridizing at 50° C. to 65° C. in 5X SSPE and 50% formamide, and washing at 50° C. to 65° C. in 0.5X SSPE; typical low stringency conditions comprise hybridizing at 35° C. to 37° C. in 5X SSPE and 40% to 45% formamide and washing at 42° C. in 1X–2X SSPE.

"SSPE" denotes a hybridization and wash solution comprising sodium chloride, sodium phosphate, and EDTA, at pH 7.4. A 20X solution of SSPE is made by dissolving 174 g of NaCl, 27.6 g of NaH2PO4.H2O, and 7.4 g of EDTA in 800 ml of H2O. The pH is adjusted with NaOH and the volume brought to 1 liter.

"SSC" denotes a hybridization and wash solution comprising sodium chloride and sodium citrate at pH 7. A 20X solution of SSC is made by dissolving 175 g of NaCl and 88 g of sodium citrate in 800 ml of H2. The volume is brought to 1 liter after adjusting the pH with 10N NaOH.

DETAILED DESCRIPTION OF THE INVENTION

The Lig gene disclosed herein (SEQ ID NO:1) and related nucleic acids encode a DNA ligase from *S. pneumoniae* that is essential for viability (SEQ ID NO:2). This gene and protein are members of the minimal gene set. The proteins categorized as "minimal gene set" counterparts are homologous to a set of highly conserved proteins found in other bacteria. The minimal gene set proteins are thought to be essential for viability and are useful targets for the development of new antibacterial compounds.

In one embodiment, the proteins of this invention are purified, and used in a screen to identify compounds that bind and/or inhibit the activity of said proteins. A variety of suitable screens are contemplated for this purpose. For example, the protein(s) can be labeled by known techniques, such as radiolabeling or fluorescent tagging, or by labeling with biotin/avidin. Thereafter, binding of a test compound to a labeled protein can be determined by any suitable means, well known to the skilled artisan.

Skilled artisans will recognize that the DNA molecules of this invention, or fragments thereof, or complements thereof, can be generated by general cloning methods. PCR amplification using oligonucleotide primers targeted to any suitable region of SEQ ID NO:l, SEQ ID NO:4, or SEQ ID NO:5 is preferred. Methods for PCR amplification are widely known in the art. See e.g. PCR Protocols: A Guide to Method and Application, Ed. M. Innis et al., Academic Press (1990) or U.S. Pat. No. 4,889,818, which hereby is incorporated by reference. A PCR comprises DNA, suitable enzymes, primers, and buffers, and is conveniently carried out in a DNA Thermal Cycler (Perkin Elmer Cetus, Norwalk, Conn.). A positive PCR result is determined by, for example, detecting an appropriately-sized DNA fragment following agarose gel electrophoresis.

The DNAs of the present invention may also be produced using synthetic methods well known in the art. (See, e.g., E. L. Brown, R. Belagaje, M. J. Ryan, and H. G. Khorana, Methods in Enzymology, 68:109–151 (1979)). An apparatus such as the Applied Biosystems Model 380A or 380B DNA synthesizers (Applied Biosystems, Inc., 850 Lincoln Center Drive, Foster City, Calif. 94404) may be used to synthesize DNA. Synthetic methods rely upon phosphotriester chemistry [See, e.g., M. J. Gait, ed., Oligonucleotide Synthesis, A Practical Approach, (1984)], or phosphoramidite chemistry.

Protein Production Methods

The present invention relates further to substantially purified proteins encoded by the gene disclosed herein.

Skilled artisans will recognize that proteins can be synthesized by different methods, for example, chemical methods or recombinant methods, as described in U.S. Pat. No. 4,617,149, which hereby is incorporated by reference.

The principles of solid phase chemical synthesis of polypeptides are well known in the art and may be found in general texts relating to this area. See, e.g., H. Dugas and C. Penney, Bioorganic Chemistry (1981) Springer-Verlag, New York, 54–92. Peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The proteins of the present invention can also be made by recombinant DNA methods. Recombinant methods are preferred if a high yield is desired. Recombinant methods involve expressing the cloned gene in a suitable host cell. The gene is introduced into the host cell by any suitable means, well known to those skilled in the art. While chromosomal integration of the cloned gene is within the scope of the present invention, it is preferred that the cloned gene be maintained extra-chromosomally, as part of a vector in which the gene is in operable-linkage to a promoter.

Recombinant methods can also be used to overproduce a membrane-bound or membrane-associated protein. In some cases, membranes prepared from recombinant cells expressing such proteins provide an enriched source of the protein.

Expressing Recombinant Proteins in Procaryotic and Eucaryotic Host Cells

Procaryotes are generally used for cloning DNA sequences and for constructing vectors. For example, the *Escherichia coli* K12 strain 294 (ATCC No. 31446) is particularly useful for expression of foreign proteins. Other strains of *E. coli,* bacilli such as *Bacillus subtilis*, enterobacteriaceae such as *Salmonella typhimurium* or *Serratia marcescans*, various Pseudomonas species may also be employed as host cells in cloning and expressing the recombinant proteins of this invention. Also contemplated are various strains of Streptococcus and Streptocmyces.

For effective recombinant protein production, a gene must be linked to a promoter sequence. Suitable bacterial promoters include b -lactamase [e.g. vector pGX2907, ATCC 39344, contains a replicon and b -lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695)] designed for the expression of a trpE fusion protein. Hybrid promoters such as the tac promoter (isolatable from plasmid pDR540, ATCC-37282) are also suitable. Promoters for use in bacterial systems also will contain a Shine-Dalgarno sequence, operably linked to the DNA encoding the desired polypeptides. These examples are illustrative rather than limiting.

A variety of mammalian cells and yeasts are also suitable hosts. The yeast *Saccharomyces cerevisiae* is commonly used. Other yeasts, such as *Kluyveromyces lactis*, are also suitable. For expression of recombinant genes in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene, a selectable marker for a trpl mutant.

Purification of Recombinantly-Produced Protein

An expression vector carrying a nucleic acid or gene of the present invention is transformed or transfected into a suitable host cell using standard methods. Cells that contain the vector are propagated under conditions suitable for expression of a recombinant protein. For example, if the gene is under the control of an inducible promoter, then suitable growth conditions would incorporate the appropriate inducer. The recombinantly-produced protein may be purified from cellular extracts of transformed cells by any suitable means.

In a preferred process for protein purification a gene is modified at the 5' end, or at some other position, such that the encoded protein incorporates several histidine residues (viz. "histidine tag"). This "histidine tag" enables "immobilized metal ion affinity chromatography" (IMAC), a single-step protein purification method described in U.S. Pat. No. 4,569,794, which hereby is incorporated by reference. The IMAC method enables isolation of substantially pure protein starting from a crude cellular extract.

As skilled artisans will recognize, owing to the degeneracy of the code, the proteins of the invention can be encoded by a large genus of different nucleic acid sequences. This invention further comprises said genus.

The ribonucleic acid compounds of the invention may be prepared using the polynucleotide synthetic methods discussed supra, or they may be prepared enzymatically using RNA polymerase to transcribe a DNA template.

The most preferred systems for preparing the ribonucleic acids of the present invention employ the RNA polymerase from the bacteriophage T7 or the bacteriophage SP6. These RNA polymerases are highly specific, requiring the insertion of bacteriophage-specific sequences at the 5' end of a template. See, J. Sambrook, et al., supra, at 18.82–18.84.

This invention also provides nucleic acids that are complementary to the sequences disclosed herein.

The present invention also provides probes and primers, useful for a variety of molecular biology techniques including, for example, hybridization screens of genomic or subgenomic libraries, or detection and quantification of MRNA species as a means to analyze gene expression. A nucleic acid compound is provided comprising any of the sequences disclosed herein, or a complementary sequence thereof, or a fragment thereof, which is at least 15 base pairs in length, and which will hybridize selectively to *Streptococcus pneumoniae* DNA or mRNA. Preferably, the 15 or more base pair compound is DNA. A probe or primer length of at least 15 base pairs is dictated by theoretical and practical considerations. See e.g. B. Wallace and G. Miyada, "Oligonucleotide Probes for the Screening of Recombinant DNA Libraries," In Methods in Enzymology, Vol. 152, 432–442, Academic Press (1987).

The probes and primers of this invention can be prepared by methods well known to those skilled in the art (See e.g. Sambrook et al. supra). In a preferred embodiment the probes and primers are synthesized by the polymerase chain reaction (PCR).

The present invention also relates to recombinant DNA cloning vectors and expression vectors comprising the nucleic acids of the present invention. Preferred nucleic acid vectors are those that comprise DNA. The skilled artisan understands that choosing the most appropriate cloning vector or expression vector depends on the availability of restriction sites, the type of host cell into which the vector is to be transfected or transformed, the purpose of transfection or transformation (e.g., stable transformation as an extrachromosomal element, or integration into a host chromosome), the presence or absence of readily assayable or selectable markers (e.g., antibiotic resistance and metabolic markers of one type and another), and the number of gene copies desired in the host cell.

Suitable vectors comprise RNA viruses, DNA viruses, lytic bacteriophages, lysogenic bacteriophages, stable bacteriophages, plasmids, viroids, and the like. The most preferred vectors are plasmids.

Host cells harboring the nucleic acids disclosed herein are also provided by the present invention. A preferred host is E. coli transfected or transformed with a vector comprising a nucleic acid of the present invention.

The invention also provides a host cell capable of expressing a gene described herein, said method comprising transforming or otherwise introducing into a host cell a recombinant DNA vector comprising an isolated DNA sequence that encodes said gene. The preferred host cell is any strain of E. coli that can accommodate high level expression of an exogenously introduced gene. Transformed host cells are cultured under conditions well known to skilled artisans, such that said gene is expressed, thereby producing the encoded protein in the recombinant host cell.

To discover compounds having antibacterial activity, one can look for agents that inhibit cell growth and/or viability by, for example, inhibiting enzymes required for cell wall biosynthesis, and/or by identifying agents that interact with membrane proteins. A method for identifying such compounds comprises contacting a suitable protein or membrane preparation with a test compound and monitoring by any suitable means an interaction and/or inhibition of a protein of this invention.

For example, the instant invention provides a screen for compounds that interact with the proteins of the invention, said screen comprising:

a) preparing a protein, or membranes enriched in a protein;

b) exposing the protein or membranes to a test compound; and c) detecting an interaction of a protein with said compound by any suitable means.

The screening method of this invention may be adapted to automated procedures such as a PANDEX® (Baxter-Dade Diagnostics) system, allowing for efficient high-volume screening of compounds.

In a typical screen, a protein is prepared as described herein, preferably using recombinant DNA technology. A test compound is introduced into a reaction vessel containing said protein. The reaction/interaction of said protein and said compound is monitored by any suitable means. In a preferred method, a radioactively-labeled or chemically-labeled compound or protein is used. A specific association between the test compound and protein is monitored by any suitable means.

In such a screening protocol Lig is prepared as described herein, preferably using recombinant DNA technology. A test compound is introduced into a reaction vessel containing the Lig protein or fragment thereof. Binding of Lig by a test compound is determined by any suitable means. For example, in one method radioactively-labeled or chemically-labeled test compound may be used. Binding of the protein by the compound is assessed, for example, by quantifying bound label versus unbound label using any suitable method. Binding of a test compound may also be carried out by a method disclosed in U.S. Pat. No. 5,585,277, which hereby is incorporated by reference. In this method, binding of a test compound to a protein is assessed by monitoring the ratio of folded protein to unfolded protein, for example by monitoring sensitivity of said protein to a protease, or amenability to binding of said protein by a specific antibody against the folded state of the protein.

The foregoing screening methods are useful for identifying a ligand of a Lig protein, perhaps as a lead to a pharmaceutical compound for modulating the state of differentiation of an appropriate tissue. A ligand that binds Lig, or related fragment thereof, is identified, for example, by combining a test ligand with Lig under conditions that cause the protein to exist in a ratio of folded to unfolded states. If the test ligand binds the folded state of the protein, the relative amount of folded protein will be higher than in the case of a test ligand that does not bind the protein. The ratio of protein in the folded versus unfolded state is easily determinable by, for example, susceptibility to digestion by a protease, or binding to a specific antibody, or binding to chaperonin protein, or binding to any suitable surface.

The following examples more fully describe the present invention. Those skilled in the art will recognize that the particular reagents, equipment, and procedures described are merely illustrative and are not intended to limit the present invention in any manner.

EXAMPLE 1

Production of a Vector for Expressing *S. pneumoniae* Lig in a Host Cell

An expression vector suitable for expressing is. pneumoniaeLig in a variety of procaryotic host cells, such as *E. coli,* is easily made. The vector contains an origin of replication (Ori), an ampicillin resistance gene (Amp) useful for selecting cells which have incorporated the vector following a tranformation procedure, and further comprises the T7 promoter and T7 terminator sequences in operable linkage to the Lig coding region. Plasmid pET11A (obtained from Novogen, Madison, Wis.) is a suitable parent plasmid. pET11A is linearized by restriction with endonucleases NdeI and BamHI. Linearized pET11A is ligated to a DNA fragment bearing NdeI and BamHI sticky ends and comprising the coding region of the *S. pneumoniae* Lig (SEQ ID NO:1). The coding region for Lig is easily produced by PCR technology using suitably designed primers to the ends of the coding region specified in SEQ ID NO:1.

The Lig gene used in this construction is slightly modified at the 5' end (amino terminus of encoded protein) in order to simplify purification of the encoded protein product. For this purpose, an oligonucleotide encoding 8 histidine residues is inserted after the ATG start codon. Placement of the histidine residues at the amino terminus of the encoded protein serves to enable the IMAC one-step protein purification procedure.

EXAMPLE 2

Recombinant Expression and Purification of a Protein Encoded by *S. pneumoniae* Lig An expression vector that carries Lig from the *S. pneumoniae* genome as disclosed herein and which Lig is operably-linked to an expression promoter is transformed into *E. coli* BL21 (DE3)(hsdS gal lcIts857 ind1Sam7nin5lacUV5-T7gene 1) using standard methods (see Example 4). Transformants, selected for resistance to ampicillin, are chosen at random and tested for the presence of the vector by agarose gel electrophoresis using quick plasmid preparations. Colonies which contain the vector are grown in L broth and the protein product encoded by the vector-borne ORF is purified by immobilized metal ion affinity chromatography (IMAC), essentially as described in U.S. Pat. No. 4,569,794.

Briefly, the IMAC column is prepared as follows. A metal-free chelating resin (e.g. Sepharose 6B IDA, Pharmacia) is washed in distilled water to remove preservative substances and infused with a suitable metal ion [e.g. Ni(II), Co(II), or Cu(II)] by adding a 50mM metal chloride or metal sulfate aqueous solution until about 75% of the interstitial spaces of the resin are saturated with colored metal ion. The column is then ready to receive a crude cellular extract containing the recombinant protein product.

After removing unbound proteins and other materials by washing the column with any suitable buffer, pH 7.5, the bound protein is eluted in any suitable buffer at pH 4.3, or preferably with an imidizole-containing buffer at pH 7.5.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
(A) LENGTH: 1959 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 1..1959

(xi) SEQUENCE DESCRIPTION: SEQ ID NO:1:

```
ATG AAT AAA AGA ATG AAT GAG TTA GTC GCT TTG CTC AAT CGC TAT GCG       48
Met Asn Lys Arg Met Asn Glu Leu Val Ala Leu Leu Asn Arg Tyr Ala
  1               5                  10                  15

ACT GAG TAC TAT ACC AGC GAT AAT CCC TCG GTT TCA GAC AGT GAG TAT       96
Thr Glu Tyr Tyr Thr Ser Asp Asn Pro Ser Val Ser Asp Ser Glu Tyr
             20                  25                  30

GAC CGC CTT TAC CGT GAG TTG GTC GAG TTA GAA ACT GCT TAT CCA GAG      144
Asp Arg Leu Tyr Arg Glu Leu Val Glu Leu Glu Thr Ala Tyr Pro Glu
         35                  40                  45

CAA GTG CTA GCA GAC AGT CCG ACT CAT CGT GTT GGT GGC AAG GTT TTA      192
Gln Val Leu Ala Asp Ser Pro Thr His Arg Val Gly Gly Lys Val Leu
     50                  55                  60

GAT GGT TTT GAA AAA TAC AGT CAT CAG TAT CCT CTT TAT AGT TTG CAG      240
Asp Gly Phe Glu Lys Tyr Ser His Gln Tyr Pro Leu Tyr Ser Leu Gln
 65                  70                  75                  80

GAT GCT TTT TCA CGT GAG GAG CTA GAT GCT TTT GAT GCG CGT GTT CGT      288
Asp Ala Phe Ser Arg Glu Glu Leu Asp Ala Phe Asp Ala Arg Val Arg
                 85                  90                  95

AAG GAA GTG GCT CAT CCG ACC TAT ATT TGT GAG CTG AAA ATC GAT GGC      336
Lys Glu Val Ala His Pro Thr Tyr Ile Cys Glu Leu Lys Ile Asp Gly
            100                 105                 110

TTA TCT ATC TCG CTG ACT TAT GAA AAG GGG ATT TTG GTT GCT GGG GTA      384
Leu Ser Ile Ser Leu Thr Tyr Glu Lys Gly Ile Leu Val Ala Gly Val
        115                 120                 125

ACA CGT GGA GAT GGT TCA ATT GGT GAA AAT ATC ACA GAA AAC CTC AAG      432
Thr Arg Gly Asp Gly Ser Ile Gly Glu Asn Ile Thr Glu Asn Leu Lys
    130                 135                 140

CGT GTT AAG GAC ATC CCT TTG ACT TTG CCA GAA GAA CTA GAT ATC ACA      480
Arg Val Lys Asp Ile Pro Leu Thr Leu Pro Glu Glu Leu Asp Ile Thr
145                 150                 155                 160

GTT CGT GGG GAA TGT TAC ATG CCA CGC GCT TCC TTT GAC CAA GTT AAC      528
```

-continued

```
Val Arg Gly Glu Cys Tyr Met Pro Arg Ala Ser Phe Asp Gln Val Asn
                165                 170                 175

CAA GCG CGC CAA GAA AAT GGA GAG CCT GAA TTT GCT AAT CCT CGT AAT      576
Gln Ala Arg Gln Glu Asn Gly Glu Pro Glu Phe Ala Asn Pro Arg Asn
            180                 185                 190

GCG GCA GCA GGA ACT CTG CGT CAG TTG GAT ACA GCA GTA GTT GCC AAG      624
Ala Ala Ala Gly Thr Leu Arg Gln Leu Asp Thr Ala Val Val Ala Lys
        195                 200                 205

CGT AAT CTT GCA ACG TTT CTC TAT CAA GAA GCC AGC CCT TCA ACT CGT      672
Arg Asn Leu Ala Thr Phe Leu Tyr Gln Glu Ala Ser Pro Ser Thr Arg
    210                 215                 220

GAT AGC CAA GAA AAG GGT TTG AAG TAC CTA GAA CAA CTA GGT TTT GTG      720
Asp Ser Gln Glu Lys Gly Leu Lys Tyr Leu Glu Gln Leu Gly Phe Val
225                 230                 235                 240

GTC AAT CCT AAG CGA ATC TTG GCT GAA AAC ATA GAT GAA ATC TGG AAT      768
Val Asn Pro Lys Arg Ile Leu Ala Glu Asn Ile Asp Glu Ile Trp Asn
                245                 250                 255

TTT ATC CAA GAA GTA GGA CAG GAA CGG GAA AAT CTG CCT TAC GAT ATT      816
Phe Ile Gln Glu Val Gly Gln Glu Arg Glu Asn Leu Pro Tyr Asp Ile
            260                 265                 270

GAT GGA GTG GTA ATC AAG GTC AAC GAC CTA GCA AGT CAA GAA GAA CTT      864
Asp Gly Val Val Ile Lys Val Asn Asp Leu Ala Ser Gln Glu Glu Leu
        275                 280                 285

GGT TTT ACC GTT AAG GCT CCA AAG TGG GCA GTA GCC TAC AAG TTC CCT      912
Gly Phe Thr Val Lys Ala Pro Lys Trp Ala Val Ala Tyr Lys Phe Pro
    290                 295                 300

GCT GAA GAA AAA GAA GCT CAA CTC TTA TCA GTT GAC TGG ACA GTT GGC      960
Ala Glu Glu Lys Glu Ala Gln Leu Leu Ser Val Asp Trp Thr Val Gly
305                 310                 315                 320

CGT ACC GGT GTT GTA ACT CCA ACT GCT AAT CTA ACA CCA GTA CAA CTT     1008
Arg Thr Gly Val Val Thr Pro Thr Ala Asn Leu Thr Pro Val Gln Leu
                325                 330                 335

GCC GGT ACG ACT GTT AGC CGT GCG ACC CTG CAC AAT GTA GAT TAT ATT     1056
Ala Gly Thr Thr Val Ser Arg Ala Thr Leu His Asn Val Asp Tyr Ile
            340                 345                 350

GCT GAA AAA GAT ATC CGA AAA GAC GAT ACG GTC ATT GTA TAT AAG GCT     1104
Ala Glu Lys Asp Ile Arg Lys Asp Asp Thr Val Ile Val Tyr Lys Ala
        355                 360                 365

GGT GAC ATC ATC CCT GCC GTT TTA CGT GTG GTA GAG TCC AAA CGG GTT     1152
Gly Asp Ile Ile Pro Ala Val Leu Arg Val Val Glu Ser Lys Arg Val
    370                 375                 380

TCT GAA GAA AAA CTA GAT ATC CCT ACA AAC TGT CCA AGT TGT AAC TCT     1200
Ser Glu Glu Lys Leu Asp Ile Pro Thr Asn Cys Pro Ser Cys Asn Ser
385                 390                 395                 400

GAC TTG TTG CAC TTT GAA GAT GAA GTG GCC CTA CGT TGT ATC AAT CCG     1248
Asp Leu Leu His Phe Glu Asp Glu Val Ala Leu Arg Cys Ile Asn Pro
                405                 410                 415

CGT TGC CCT GCT CAA ATC ATG GAA GGC TTG ATT CAC TTT GCT TCT CGT     1296
Arg Cys Pro Ala Gln Ile Met Glu Gly Leu Ile His Phe Ala Ser Arg
            420                 425                 430

GAT GCT ATG AAT ATT ACA GGC CTT GGT CCA TCT ATT GTT GAG AAG CTT     1344
Asp Ala Met Asn Ile Thr Gly Leu Gly Pro Ser Ile Val Glu Lys Leu
        435                 440                 445

TTT GCT GCT AAT TTA GTC AAG GAT GTG GCG GAT ATT TAT CGT TTG CAA     1392
Phe Ala Ala Asn Leu Val Lys Asp Val Ala Asp Ile Tyr Arg Leu Gln
    450                 455                 460

GAA GAG GAT TTC CTC CTT TTA GAG GGG GTT AAG GAA AAG TCC GCT GCT     1440
Glu Glu Asp Phe Leu Leu Leu Glu Gly Val Lys Glu Lys Ser Ala Ala
465                 470                 475                 480
```

-continued

```
AAA CTG TAT CAG GCT ATC CAA GCA TCA AAG GAA AAT TCT GCC GAG AAG     1488
Lys Leu Tyr Gln Ala Ile Gln Ala Ser Lys Glu Asn Ser Ala Glu Lys
                485                 490                 495

CTC TTA TTT GGT TTG GGA ATT CGT CAT GTC GGA AGC AAG GCT AGT CAG     1536
Leu Leu Phe Gly Leu Gly Ile Arg His Val Gly Ser Lys Ala Ser Gln
            500                 505                 510

CTT TTA CTT CAA TAT TTC CAT TCA ATT GAA AAT CTG TAT CAG GCA GAT     1584
Leu Leu Leu Gln Tyr Phe His Ser Ile Glu Asn Leu Tyr Gln Ala Asp
        515                 520                 525

TCA GAG GAA GTG GCT AGT ATT GAA AGT CTA GGT GGC GTG ATT GCC AAA     1632
Ser Glu Glu Val Ala Ser Ile Glu Ser Leu Gly Gly Val Ile Ala Lys
    530                 535                 540

AGT CTT CAG ACT TAT TTT GCG GCA GAA GGC TCT GAA ATT CTG CTC AGA     1680
Ser Leu Gln Thr Tyr Phe Ala Ala Glu Gly Ser Glu Ile Leu Leu Arg
545                 550                 555                 560

GAA TTG AAA GAA ACT GGG GTC AAT CTG GAC TAT AAA GGA CAG ACG GTA     1728
Glu Leu Lys Glu Thr Gly Val Asn Leu Asp Tyr Lys Gly Gln Thr Val
                565                 570                 575

GTA GCG GAT GCG GCC TTG TCA GGT TTG ACC GTG GTA TTG ACA GGA AAA     1776
Val Ala Asp Ala Ala Leu Ser Gly Leu Thr Val Val Leu Thr Gly Lys
            580                 585                 590

TTG GAA CGA CTC AAG CGC TCA GAA GCT AAA AGT AAA CTC GAA AGT CTG     1824
Leu Glu Arg Leu Lys Arg Ser Glu Ala Lys Ser Lys Leu Glu Ser Leu
        595                 600                 605

GGT GCC AAA GTG ACA GGT AGT GTT TCT AAA AAG ACC GAC CTC GTC GTG     1872
Gly Ala Lys Val Thr Gly Ser Val Ser Lys Lys Thr Asp Leu Val Val
    610                 615                 620

GTA GGT GCA GAC GCT GGA AGT AAA CTG CAA AAA GCA CAA GAA CTT GGT     1920
Val Gly Ala Asp Ala Gly Ser Lys Leu Gln Lys Ala Gln Glu Leu Gly
625                 630                 635                 640

ATC CAG GTC AGA GAT GAG GCA TGG CTA GAA AGT TTG TAA                 1959
Ile Gln Val Arg Asp Glu Ala Trp Leu Glu Ser Leu  *
                645                 650
```

(2) INFORMATION FOR SEQ ID NO:2:

(i) SEQUENCE CHARACTERISTICS:
(A) LENGTH: 652 amino acids
(B) TYPE: amino acid
(D) TOPOLOGY: linear (ii) MOLECULE TYPE: protein (xi) SEQUENCE DESCRIPTION: SEQ ID NO:2:

```
Met Asn Lys Arg Met Asn Glu Leu Val Ala Leu Leu Asn Arg Tyr Ala
  1               5                  10                  15

Thr Glu Tyr Tyr Thr Ser Asp Asn Pro Ser Val Ser Asp Ser Glu Tyr
             20                  25                  30

Asp Arg Leu Tyr Arg Glu Leu Val Glu Leu Glu Thr Ala Tyr Pro Glu
         35                  40                  45

Gln Val Leu Ala Asp Ser Pro Thr His Arg Val Gly Gly Lys Val Leu
     50                  55                  60

Asp Gly Phe Glu Lys Tyr Ser His Gln Tyr Pro Leu Tyr Ser Leu Gln
 65                  70                  75                  80

Asp Ala Phe Ser Arg Glu Glu Leu Asp Ala Phe Asp Ala Arg Val Arg
                 85                  90                  95

Lys Glu Val Ala His Pro Thr Tyr Ile Cys Glu Leu Lys Ile Asp Gly
            100                 105                 110

Leu Ser Ile Ser Leu Thr Tyr Glu Lys Gly Ile Leu Val Ala Gly Val
        115                 120                 125
```

-continued

```
Thr Arg Gly Asp Gly Ser Ile Gly Glu Asn Ile Thr Glu Asn Leu Lys
    130                 135                 140

Arg Val Lys Asp Ile Pro Leu Thr Leu Pro Glu Glu Leu Asp Ile Thr
145                 150                 155                 160

Val Arg Gly Glu Cys Tyr Met Pro Arg Ala Ser Phe Asp Gln Val Asn
                165                 170                 175

Gln Ala Arg Gln Glu Asn Gly Glu Pro Glu Phe Ala Asn Pro Arg Asn
            180                 185                 190

Ala Ala Ala Gly Thr Leu Arg Gln Leu Asp Thr Ala Val Val Ala Lys
        195                 200                 205

Arg Asn Leu Ala Thr Phe Leu Tyr Gln Glu Ala Ser Pro Ser Thr Arg
    210                 215                 220

Asp Ser Gln Glu Lys Gly Leu Lys Tyr Leu Glu Gln Leu Gly Phe Val
225                 230                 235                 240

Val Asn Pro Lys Arg Ile Leu Ala Glu Asn Ile Asp Glu Ile Trp Asn
                245                 250                 255

Phe Ile Gln Glu Val Gly Gln Glu Arg Glu Asn Leu Pro Tyr Asp Ile
            260                 265                 270

Asp Gly Val Val Ile Lys Val Asn Asp Leu Ala Ser Gln Glu Glu Leu
        275                 280                 285

Gly Phe Thr Val Lys Ala Pro Lys Trp Ala Val Ala Tyr Lys Phe Pro
    290                 295                 300

Ala Glu Glu Lys Glu Ala Gln Leu Leu Ser Val Asp Trp Thr Val Gly
305                 310                 315                 320

Arg Thr Gly Val Val Thr Pro Thr Ala Asn Leu Thr Pro Val Gln Leu
                325                 330                 335

Ala Gly Thr Thr Val Ser Arg Ala Thr Leu His Asn Val Asp Tyr Ile
            340                 345                 350

Ala Glu Lys Asp Ile Arg Lys Asp Asp Thr Val Ile Val Tyr Lys Ala
        355                 360                 365

Gly Asp Ile Ile Pro Ala Val Leu Arg Val Val Glu Ser Lys Arg Val
    370                 375                 380

Ser Glu Glu Lys Leu Asp Ile Pro Thr Asn Cys Pro Ser Cys Asn Ser
385                 390                 395                 400

Asp Leu Leu His Phe Glu Asp Glu Val Ala Leu Arg Cys Ile Asn Pro
                405                 410                 415

Arg Cys Pro Ala Gln Ile Met Glu Gly Leu Ile His Phe Ala Ser Arg
            420                 425                 430

Asp Ala Met Asn Ile Thr Gly Leu Gly Pro Ser Ile Val Glu Lys Leu
        435                 440                 445

Phe Ala Ala Asn Leu Val Lys Asp Val Ala Asp Ile Tyr Arg Leu Gln
    450                 455                 460

Glu Glu Asp Phe Leu Leu Leu Glu Gly Val Lys Glu Lys Ser Ala Ala
465                 470                 475                 480

Lys Leu Tyr Gln Ala Ile Gln Ala Ser Lys Glu Asn Ser Ala Glu Lys
                485                 490                 495

Leu Leu Phe Gly Leu Gly Ile Arg His Val Gly Ser Lys Ala Ser Gln
            500                 505                 510

Leu Leu Leu Gln Tyr Phe His Ser Ile Glu Asn Leu Tyr Gln Ala Asp
        515                 520                 525

Ser Glu Glu Val Ala Ser Ile Glu Ser Leu Gly Gly Val Ile Ala Lys
    530                 535                 540
```

-continued

```
Ser Leu Gln Thr Tyr Phe Ala Ala Glu Gly Ser Glu Ile Leu Leu Arg
545                 550                 555                 560

Glu Leu Lys Glu Thr Gly Val Asn Leu Asp Tyr Lys Gly Gln Thr Val
                565                 570                 575

Val Ala Asp Ala Ala Leu Ser Gly Leu Thr Val Val Leu Thr Gly Lys
            580                 585                 590

Leu Glu Arg Leu Lys Arg Ser Glu Ala Lys Ser Lys Leu Glu Ser Leu
        595                 600                 605

Gly Ala Lys Val Thr Gly Ser Val Ser Lys Lys Thr Asp Leu Val Val
    610                 615                 620

Val Gly Ala Asp Ala Gly Ser Lys Leu Gln Lys Ala Gln Glu Leu Gly
625                 630                 635                 640

Ile Gln Val Arg Asp Glu Ala Trp Leu Glu Ser Leu
                645                 650
```

(2) INFORMATION FOR SEQ ID NO:3:

(i) SEQUENCE CHARACTERISTICS:
(A) LENGTH: 1959 base pairs
(B) TYPE: nucleic acid
(C) STRANDEDNESS: single
(D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

```
AUGAAUAAAA GAAUGAAUGA GUUAGUCGCU UUGCUCAAUC GCUAUGCGAC UGAGUACUAU     60

ACCAGCGAUA AUCCCUCGGU UUCAGACAGU GAGUAUGACC GCCUUUACCG UGAGUUGGUC    120

GAGUUAGAAA CUGCUUAUCC AGAGCAAGUG CUAGCAGACA GUCCGACUCA UCGUGUUGGU    180

GGCAAGGUUU UAGAUGGUUU UGAAAAAUAC AGUCAUCAGU AUCCUCUUUA UAGUUUGCAG    240

GAUGCUUUUU CACGUGAGGA GCUAGAUGCU UUUGAUGCGC GUGUUCGUAA GGAAGUGGCU    300

CAUCCGACCU AUAUUUGUGA GCUGAAAAUC GAUGGCUUAU CUAUCUCGCU GACUUAUGAA    360

AAGGGGAUUU UGGUUGCUGG GGUAACACGU GGAGAUGGUU CAAUUGGUGA AAAUAUCACA    420

GAAAACCUCA AGCGUGUUAA GGACAUCCCU UUGACUUUGC CAGAAGAACU AGAUAUCACA    480

GUUCGUGGGG AAUGUUACAU GCCACGCGCU UCCUUUGACC AAGUUAACCA AGCGCGCCAA    540

GAAAAUGGAG AGCCUGAAUU UGCUAAUCCU CGUAAUGCGG CAGCAGGAAC UCUGCGUCAG    600

UUGGAUACAG CAGUAGUUGC CAAGCGUAAU CUUGCAACGU UUCUCUAUCA AGAAGCCAGC    660

CCUUCAACUC GUGAUAGCCA AGAAAAGGGU UUGAAGUACC UAGAACAACU AGGUUUUGUG    720

GUCAAUCCUA AGCGAAUCUU GGCUGAAAAC AUAGAUGAAA UCUGGAAUUU UAUCCAAGAA    780

GUAGGACAGG AACGGGAAAA UCUGCCUUAC GAUAUUGAUG GAGUGGUAAU CAAGGUCAAC    840

GACCUAGCAA GUCAAGAAGA ACUUGGUUUU ACCGUUAAGG CUCCAAAGUG GGCAGUAGCC    900

UACAAGUUCC CUGCUGAAGA AAAAGAAGCU CAACUCUUAU CAGUUGACUG GACAGUUGGC    960

CGUACCGGUG UUGUAACUCC AACUGCUAAU CUAACACCAG UACAACUUGC CGGUACGACU   1020

GUUAGCCGUG CGACCCUGCA CAAUGUAGAU UAUAUUGCUG AAAAAGAUAU CCGAAAAGAC   1080

GAUACGGUCA UUGUAUAUAA GGCUGGUGAC AUCAUCCCUG CCGUUUUACG UGUGGUAGAG   1140

UCCAAACGGG UUUCUGAAGA AAAACUAGAU AUCCCUACAA ACUGUCCAAG UUGUAACUCU   1200

GACUUGUUGC ACUUUGAAGA UGAAGUGGCC CUACGUUGUA UCAAUCCGCG UUGCCCUGCU   1260
```

-continued

```
CAAAUCAUGG AAGGCUUGAU UCACUUUGCU UCUCGUGAUG CUAUGAAUAU UACAGGCCUU   1320

GGUCCAUCUA UUGUUGAGAA GCUUUUUGCU GCUAAUUUAG UCAAGGAUGU GGCGGAUAUU   1380

UAUCGUUUGC AAGAAGAGGA UUUCCUCCUU UUAGAGGGGG UUAAGGAAAA GUCCGCUGCU   1440

AAACUGUAUC AGGCUAUCCA AGCAUCAAAG GAAAAUUCUG CCGAGAAGCU CUUAUUUGGU   1500

UUGGGAAUUC GUCAUGUCGG AAGCAAGGCU AGUCAGCUUU UACUUCAAUA UUUCCAUUCA   1560

AUUGAAAAUC UGUAUCAGGC AGAUUCAGAG GAAGUGGCUA GUAUUGAAAG UCUAGGUGGC   1620

GUGAUUGCCA AAAGUCUUCA GACUUAUUUU GCGGCAGAAG GCUCUGAAAU UCUGCUCAGA   1680

GAAUUGAAAG AAACUGGGGU CAAUCUGGAC UAUAAAGGAC AGACGGUAGU AGCGGAUGCG   1740

GCCUUGUCAG GUUUGACCGU GGUAUUGACA GGAAAAUUGG AACGACUCAA GCGCUCAGAA   1800

GCUAAAAGUA AACUCGAAAG UCUGGGUGCC AAAGUGACAG GUAGUGUUUC UAAAAAGACC   1860

GACCUCGUCG UGGUAGGUGC AGACGCUGGA AGUAAACUGC AAAAAGCACA AGAACUUGGU   1920

AUCCAGGUCA GAGAUGAGGC AUGGCUAGAA AGUUUGUAA                          1959
```

(2) INFORMATION FOR SEQ ID NO:4:

(i) SEQUENCE CHARACTERISTICS:
(A) LENGTH: 1557 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
TTTCAGCTCA CAAATATAGG TCGGATGAGC CACTTCCTTA CGAACACGCG CATCAAAAGC     60

ATCTAGCTCC TCACGTGAAA AAGCATCCTG CAAACTATAA AGAGGATACT GATGACTGTA    120

TTTTTCAAAA CCATCTAAAA CCTTGCCACC AACACGATGA GTCGGACTGT CTGCTAGCAC    180

TTGCTCTGGA TAAGCAGTTT CTAACTCGAC CAACTCACGG TAAAGGCGGT CATACTCACT    240

GTCTGAAACC GAGGGATTAT CGCTGGTATA GTACTCAGTC GCATAGCGAT TGAGCAAAGC    300

GACTAACTCA TTCATTCTTT TATTCATAAG ACCATTTTAC CATAAAACAA GCCCTCCTCA    360

CAAACGAGAA GGGCGGAAAA AACACTTAGT TTGAAATTAT TTTTGAAACT CAAGCAACCT    420

TATATCAATT TTTCAAAATG AGTTCGAACA TAAATAAACG ATATACAAGA CAAGATGATA    480

ACACCACTTC CAATTATCAG GAAAGAAGAG AGATGTACAC TTGGCAAGAC TGTCATAAAT    540

CCTTTTGCAA TAGGCATAAA TAGAATAGCT AAGGTAAAAA TTGTACTCAG TACTCTTCCA    600

AGAAATTCGC TCTCAACCTT GGTTTGTACT TGAGTAAAAA AGTGAATATT AAAAATCGTC    660

ATAAACAATT CACAAACTAA ATTTCCAGAA AAGGAAAGAA AAGTTGGAAG TGGTAATCCC    720

ATCATAAAAA CTCCGACACC TGTCAAAGCC AGTAAAATCA AAAGATTATA AATATTAGCT    780

TTAATTTTAC TAGCTAGAAG AGCCCCAATG ATGGAACCAA TAGCCCCCAT AGTTAAAATA    840

CTTGCATAGG CTCCTTCTGA CCCGTAAAGC TGATTCGAAA AGGGAAGTAG AAATTCAAAA    900

GCTGCAAAAA AGAAATTAAC GCTGGAAGCT ACCAGCAAAA GGAAGAAAAT TTCTTGCTGA    960

TGCCAGATAT AGTGTAACCC ATCCTTGATA TCTACAAAAA TATCTCTCCC AGTAAAAGCC   1020

TTTTTCTCTT GAACTTTTGC TTCCTCTTTT GGAAGGAAAG CCACTAGAAC AAAAGCAATG   1080

AAAAAAGTCA GCGAGTCTAG CAGTAGCGTC ATATGGAGAC TTGCAAACTG TAAAACAAGG   1140
```

-continued

```
AAGGAAAGAA CAGGAGAGCT AACACCTACA ACCTGCAAAA CCAGCTCTAA GCGAGAATTA   1200

TAGATCACAA TCTCATTTTT CTCCACCACT TCAGTTATGA TAGCTTTATT GGCTGTGCGA   1260

GAAAAGGCAA AAGCAATAGC CTGCACAATG TTAGCAACAA TCAAAGCGCC AATCATCCAG   1320

CTATCATTCC TTATGAAAGA AATAGCCAGA CAAAGAATCC CACAAACAAG ATCTGCCGTC   1380

ATTAAAATCT TACGACGAGA AAAACGGTCT GAAATAACTC CGCCAAAGGG ATTGACGAGA   1440

ATAGATGTGA CGAGCTCAGA AATCTGATAC ATTCCTAAAA CTGTCTGTCC TATAGTCCCC   1500

ATAGAAGCCA ACCAGACACT ATTTCCATAA TCATAGAGCA TATTCCCATT TTATTGA      1557
```

```
(2) INFORMATION FOR SEQ ID NO:5:

     (i) SEQUENCE CHARACTERISTICS:
          (A) LENGTH: 658 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (xi) SEQUENCE DESCRIPTION: SEQ ID NO:5:

CTTATTTGGT TTGGGAATTC GTCATGTCGG AAGCAAGGCT AGTCAGCTTT TACTTCAATA     60

TTTCCATTCA ATTGAAAATC TGTATCAGGC AGATTCAGAG GAAGTGGCTA GTATTGAAAG    120

TCTAGGTGGC GTGATTGCCA AAAGTCTTCA GACTTATTTT GCGGCAGAAG GCTCTGAAAT    180

TCTGCTCAGA GAATTGAAAG AAACTGGGGT CAATCTGGAC TATAAAGGAC AGACGGTAGT    240

AGCGGATGCG GCCTTGTCAG GTTTGACCGT GGTATTGACA GGAAAATTGG AACGACTCAA    300

GCGCTCAGAA GCTAAAAGTA AACTCGAAAG TCTGGGTGCC AAAGTGACAG GTAGTGTTTC    360

TAAAAAGACC GACCTCGTCG TGGTAGGTGC AGACGCTGGA AGTAAACTGC AAAAAGCACA    420

AGAACTTGGT ATCCAGGTCA GAGATGAGGC ATGGCTAGAA AGTTTGTAAT GGATCGTTTA    480

AAAACAGAGT TTAGAGAATA TGACTATGTC TGTTAATTGA GACGAGATTG ACAAAAATTT    540

ATTAGTGAAA TAGGAAACAA AGTAAAAAGG AAAAATAAAA AATGTATACT ACCCTATGCG    600

CATTCATTAC CATCGTAAGA ATGGAGAATA TGACCTTGCT CCTTTGTAAA AGTCAGGA      658
```

We claim:

1. An isolated nucleic acid fragment, wherein said fragment has a sequence selected from the group consisting of:

(a) SEQ ID NO: 1;

(b) SEQ ID NO: 3;

(c) a nucleic acid fragment that encodes the same protein as depicted in SEQ ID NO:2; and (d) a nucleic acid fragment fully complementary to (a), (b), or (c).

2. The isolated nucleic acid fragment of claim 1, wherein the sequence of said fragment is selected from the group consisting of SEQ ID NO: 1, a nucleic acid fragment that encodes the same protein as depicted in SEQ ID NO:2 , and a nucleic acid fragment fully complementary to either of the foregoing.

3. The isolated nucleic acid fragment of claim 1, wherein the sequence of said fragment is selected from the group consisting of SEQ ID NO:3, a nucleic acid fragment that encodes the same protein as depicted in SEQ ID NO:2 , and a nucleic acid fragment fully complementary to either of the foregoing.

4. An isolated nucleic acid fragment encoding a protein having the amino acid sequence that is SEQ ID NO:2.

5. A vector comprising the isolated nucleic acid fragment of claim 4.

6. The vector of claim 5, wherein said isolated nucleic acid fragment is SEQ ID NO:1, operably-linked to a promoter sequence from said vector.

7. A recombinant host cell containing said vector of claim 6.

8. A recombinant host cell containing said vector of claim 5.

9. A method for constructing a recombinant host cell having the potential to express a protein having the amino acid sequence shown in SEQ ID NO:2, said method comprising introducing into said host cell by any suitable means said vector of claim 5.

10. A method for producing a protein having the amino acid sequence of SEQ ID NO:2 in said recombinant host cell of claim 7, said method comprising culturing the recombinant host cell under conditions suitable for production of said protein.

11. The method of claim 10, further comprising recovering said protein.

12. An isolated nucleic acid fragment, wherein said fragment consists essentially of a sequence selected from the group consisting of:

(a) SEQ ID NO: 1;

(b) SEQ ID NO: 3;

(c) a nucleic acid fragment that encodes the same protein as depicted in SEQ ID NO:2; and (d) a nucleic acid fragment fully complementary to (a), (b), or (c).

13. The isolated nucleic acid fragment of claim 12, wherein the sequence of said fragment is selected from the group consisting of:

(a) SEQ ID NO:1;

(b) a nucleic acid fragment that encodes the same protein as depicted in SEC ID NO:2 ; and (c) a nucleic acid fragment fully complementary to (a) or (b).

14. The isolated nucleic acid fragment of claim 12, wherein the sequence of said fragment is selected from the group consisting of:

(a) SEQ ID NO:3;

(b) a nucleic acid fragment that encodes the same protein as depicted in SEQ ID NO:2 ; and (c) a nucleic acid fragment fully complementary to (a) or (b).

15. An isolated nucleic acid fragment consisting essentially of a nucleotide sequence encoding a protein having the amino acid sequence that is SEQ ID NO:2.

16. A vector comprising said isolated nucleic acid fragment of claim 15.

17. The vector of claim 16, wherein said isolated nucleic acid fragment is SEQ ID NO:1, operably linked to a promoter sequence from said vector.

18. A recombinant host cell containing said vector of claim 17.

19. A recombinant host cell containing said vector of claim 16.

20. A method for constructing a recombinant host cell having the potential to express a protein having the amino acid sequence shown in SEQ ID NO:2, said method comprising introducing into said host cell by any suitable means said vector of claim 16.

21. A method for producing a protein having the amino acid sequence of SEQ ID NO:2 in the recombinant host cell of claim 18, said method comprising culturing said recombinant host cell under conditions suitable for production of said protein.

22. The method of claim 21, further comprising recovering said protein.

* * * * *